(12) United States Patent
Gupta

(10) Patent No.: US 11,224,726 B2
(45) Date of Patent: Jan. 18, 2022

(54) HIGH-TORQUE GUIDEWIRES AND METHODS FOR MAKING AND USING THEM

(71) Applicant: SELFEX DEVICES, INC., San Leandro, CA (US)

(72) Inventor: Vikas Gupta, San Leandro, CA (US)

(73) Assignee: SELFEX DEVICES, INC., San Leandro, CA (US)

(*) Notice: Subject to any disclaimer, the term of this patent is extended or adjusted under 35 U.S.C. 154(b) by 171 days.

(21) Appl. No.: 16/292,043

(22) Filed: Mar. 4, 2019

(65) Prior Publication Data

US 2019/0192828 A1     Jun. 27, 2019

Related U.S. Application Data

(63) Continuation of application No. 15/002,381, filed on Jan. 20, 2016, now Pat. No. 10,220,189.

(Continued)

(51) Int. Cl.
*A61M 25/09* (2006.01)
*B21F 45/00* (2006.01)
(Continued)

(52) U.S. Cl.
CPC ...... *A61M 25/09* (2013.01); *A61M 25/09041* (2013.01); *B21F 45/008* (2013.01);
(Continued)

(58) Field of Classification Search
CPC .............. A61M 25/09–0905; A61M 2025/09008–09191; A61B 2017/22038
See application file for complete search history.

(56) References Cited

U.S. PATENT DOCUMENTS 4,509,945 A * 4/1985 Kramann ........... A61M 25/0111
604/164.13
5,725,534 A * 3/1998 Rasmussen ...... A61B 17/12022
600/585

(Continued)

OTHER PUBLICATIONS

Canadian Intellectual Property Office, International Search Report for corresponding International Application No. PCT/IB2016/000205, Form PCT/ISA/210, dated May 18, 2016, 6 pages.

(Continued)

*Primary Examiner* — David J. McCrosky
(74) *Attorney, Agent, or Firm* — William A. English; Vista IP Law Group LLP

(57) ABSTRACT

High torque guidewires and methods for making and using them are provided. A guidewire may include an inner core wire movable relative to an outer jacket. The outer jacket includes proximal and distal ends, a lumen extending there between, thereby defining a longitudinal axis, and one or more helical slots adjacent the distal end. The core wire includes a proximal portion, a distal portion slidably received in the outer jacket lumen and terminating in a curved distal tip that extends from the outer jacket distal end, and one or more pins on the distal portion, each pin slidably received in a respective helical slot in the outer jacket such that axial movement of the core wire relative to the outer jacket causes the pin to slide within the helical slot and rotate the distal tip relative to the outer jacket distal end.

19 Claims, 12 Drawing Sheets

Related U.S. Application Data

(60) Provisional application No. 62/105,457, filed on Jan. 20, 2015.

(51) Int. Cl.
    *A61B 17/22*         (2006.01)
    *A61B 17/3207*    (2006.01)
    *A61B 17/32*        (2006.01)

(52) U.S. Cl.
    CPC ....... *A61B 17/22* (2013.01); *A61B 17/320758* (2013.01); *A61B 2017/22038* (2013.01); *A61B 2017/22079* (2013.01); *A61B 2017/22094* (2013.01); *A61B 2017/320012* (2013.01); *A61B 2017/320733* (2013.01); *A61B 2217/005* (2013.01); *A61M 2025/09108* (2013.01); *A61M 2025/09175* (2013.01)

(56) References Cited

U.S. PATENT DOCUMENTS

| | | | | |
|---|---|---|---|---|
| 5,976,074 | A | * | 11/1999 | Moriyama ......... A61B 1/00078 600/139 |
| 9,439,664 | B2 | * | 9/2016 | Sos .................. A61B 17/22032 |
| 2013/0053766 | A1 | | 2/2013 | Hollett |

OTHER PUBLICATIONS

Canadian Intellectual Property Office, Written Opinion for corresponding International Application No. PCT/IB2016/000205, Form PCT/ISA/237, dated May 13, 2016, 6 pages.

\* cited by examiner

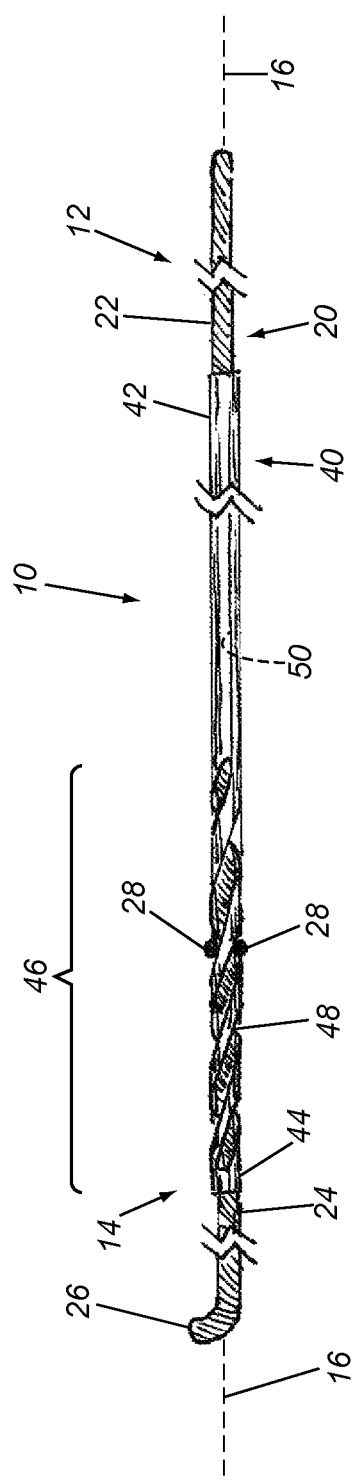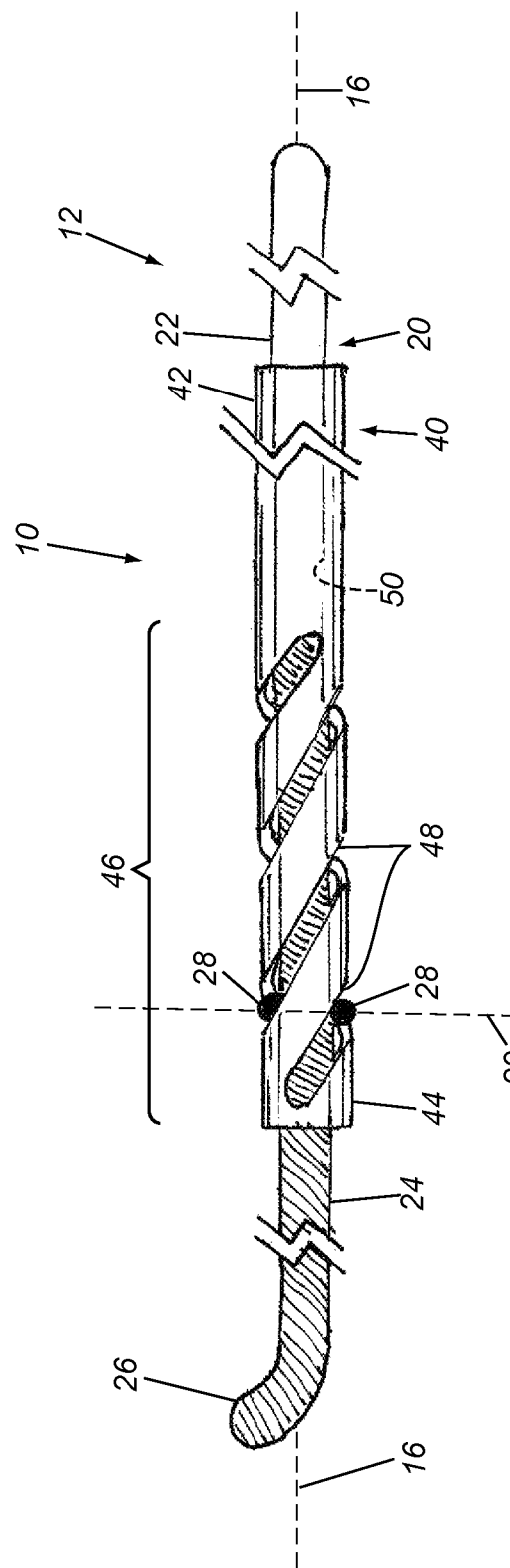

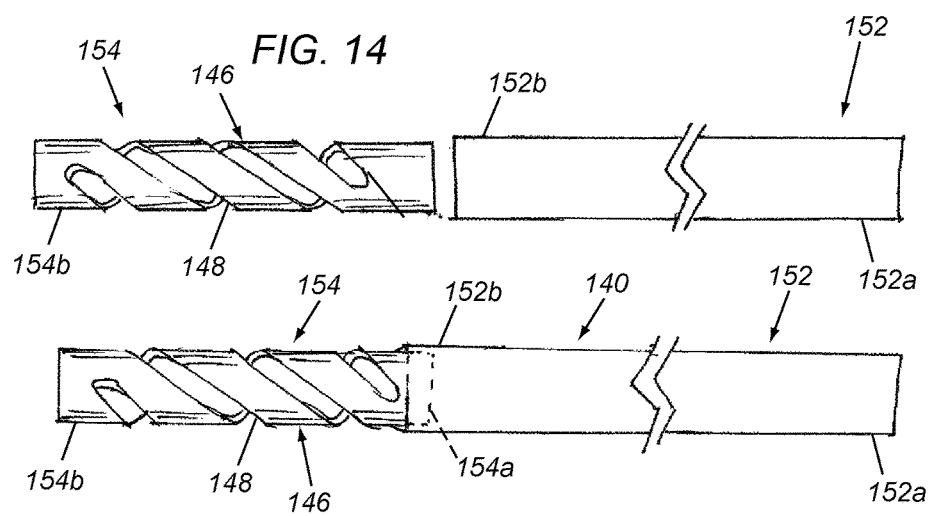
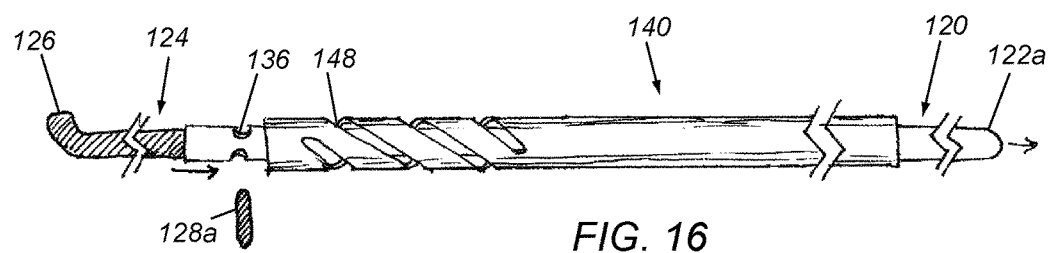
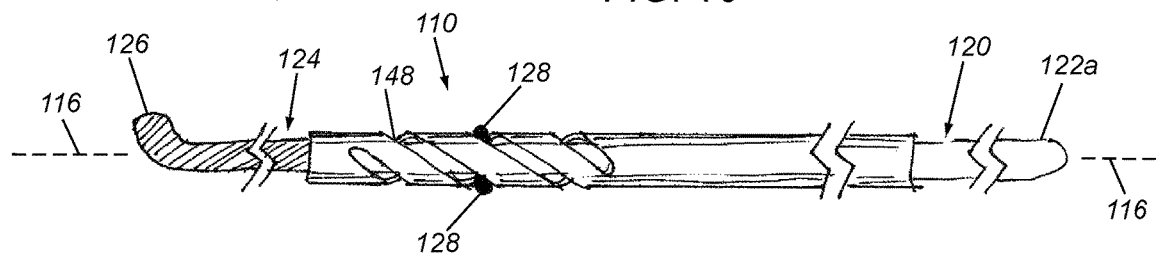

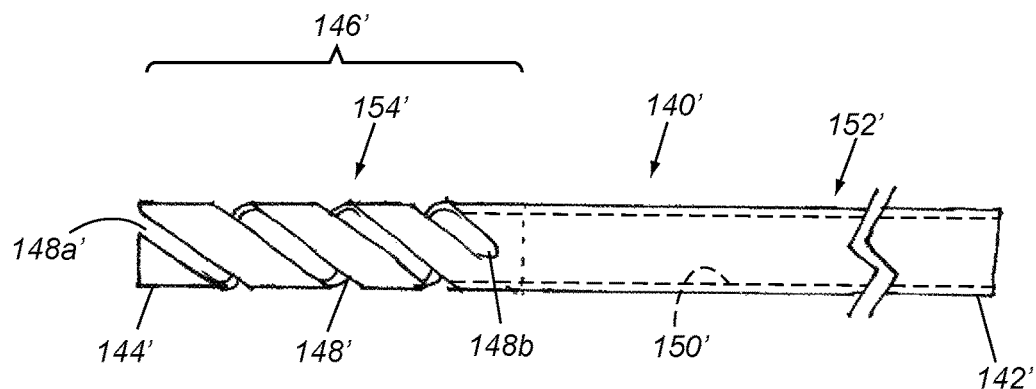
FIG. 18
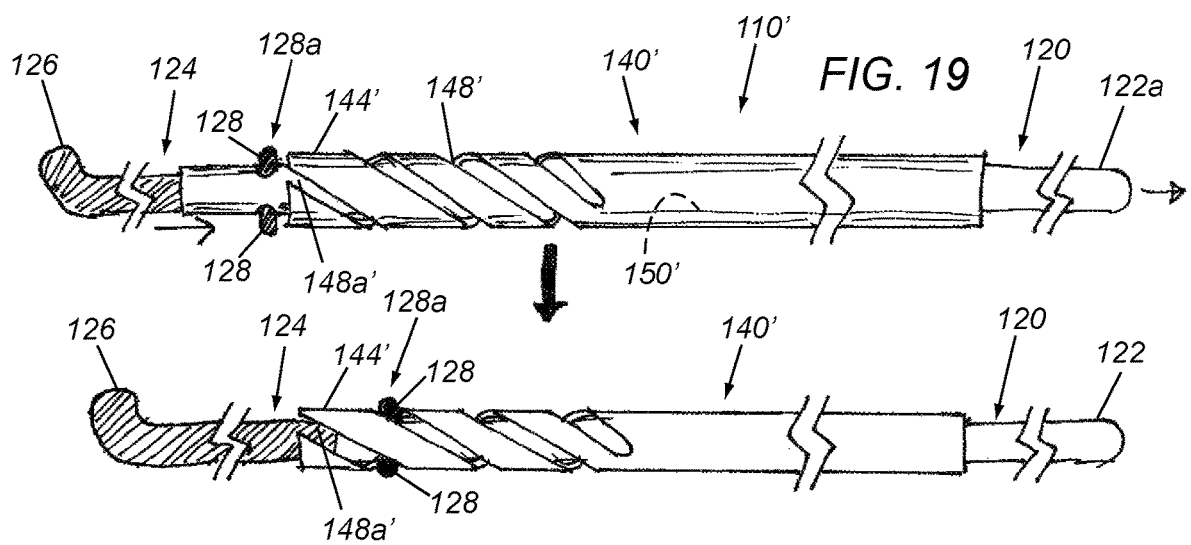
FIG. 19
FIG 20

HIGH-TORQUE GUIDEWIRES AND METHODS FOR MAKING AND USING THEM

RELATED APPLICATION DATA

The present application is a divisional of co-pending application Ser. No. 15/002,381, filed Jan. 20, 2016, and issuing as U.S. Pat. No. 10,220,189, which claims benefit of provisional application Ser. No. 62/105,457, filed Jan. 20, 2015, the entire disclosures of which are expressly incorporated by reference.

FIELD OF THE INVENTION

The present invention relates generally to guidewires and to systems and methods for making and using guidewires, and, more particularly, relates to guidewires having a distal tip with a high degree of torquabilty, e.g., for use in neurovascular applications. A torquable guidewire may facilitate a user navigating a catheter or micro-catheter safely and/or easily through the complicated blood vasculature in a human body, or may be used to break-up and/or remove a clot within a blood vessel.

BACKGROUND

A guidewire is used as a guide to track a catheter (or a micro-catheter) into targeted regions of the human vasculature or other body lumens. As the leading end of the catheter is pushed through blood vessels, it may encounter one or more branch vessels extending from a main vessel. In order for the catheter to select the correct branch vessel, the guidewire tip (which precedes the catheter tip into the main vessel) is manually torqued to select the desired branch vessel first. The catheter is then tracked over the guidewire into the selected branch vessel. This process may be repeated as desired until the catheter tip reaches the target location in the vasculature, whereupon a medical procedure may be performed.

A guidewire is a device that is made up primarily of a metallic coiled wire with a flexible leading segment. The degree of flexibility imparted to the wire depends upon the complexity of the vasculature for which it is intended. For example, a guidewire used in a neurovascular application should be highly flexible in order to maneuver through the extreme tortuosity found in the blood vessels in the brain. The two main functions of any guidewire are to 1) be able to track through tortuous blood vessels, and 2) be able to effectively select between branch vessels swiftly and effectively. Current guidewires do well in their ability to navigate through the vasculature; however, they lack in their ability to torque effectively and swiftly.

In most guidewires, typically as long as one hundred fifty centimeters (150 cm) or more, the flexible segment is constructed using two materials, namely coiled metallic wire fixed over a thin and flexible core metallic wire. Such construction provides a high degree of flexibility to the wire; however, it negatively affects the ability to torque the tip. Since one of the primary functions of the guidewire is to select branch vessels effectively, it is adversely affected by the lack of the ability to torque.

The generally practiced method of torqueing a guidewire is achieved by manually twisting a proximal end of the guidewire that remains outside of the patient's body (i.e., the user end). Due to the tortuosity of the vasculature coupled with the construction of the guidewire, the twisting of the proximal end of the guidewire at the user end does not necessarily translate proportionally to the distal end inside the body. This, in turn, may affect the user, e.g., making it difficult to access desired vessels required for the treatment.

Accordingly, there is a need for guidewires that provide both the ability to navigate inside complex and tortuous vasculature and the ability to torque a guidewire in order to select branch blood vessels swiftly and effectively.

SUMMARY

The present invention is directed to guidewires having a torquable tip and to systems and methods for making and using such guidewires. More particularly, the present invention is directed to torquable guidewires used in neurovascular applications that may facilitate a user (e.g., physician) navigating a catheter or micro-catheter over the guidewire safely and/or easily through the complicated blood vasculature in a human body, or may be used to break-up and/or remove a clot within a blood vessel.

In accordance with an exemplary embodiment, a guidewire is provided that includes an inner core wire movable relative to an outer jacket. The outer jacket may include proximal and distal ends, a lumen extending there between, thereby defining a longitudinal axis, and one or more helical slots adjacent the distal end. The core wire may include a proximal portion, a distal portion slidably received in the outer jacket lumen and terminating in a curved distal tip that extends from the outer jacket distal end, and one or more pins on the distal portion. Each pin may be slidably received in a respective helical slot in the outer jacket such that axial movement of the core wire relative to the outer jacket causes the pin to slide within the helical slot and rotate the distal tip relative to the outer jacket distal end.

In accordance with another embodiment, a method is provided for making a guidewire that includes forming an inner core wire comprising a proximal portion and a distal portion terminating in a curved distal tip; forming an outer jacket comprising a proximal portion, a distal portion sized for introduction into a patient's body and terminating at a distal end, a lumen extending there between, and a helical slot extending from an open end at the outer jacket distal end proximally and helically around the outer jacket distal portion; directing the core wire proximal portion proximally into the lumen from the outer jacket distal end until an intermediate portion of the core wire is aligned with the helical slot; and attaching a pin to the core wire intermediate portion through the helical slot such that the pin is slidable along the helical slot when the core wire is directed axially relative to the outer jacket to rotate the core wire distal tip.

In accordance with still another embodiment, a method is provided for making a guidewire that includes forming an inner core wire comprising a proximal portion, an intermediate portion, and a distal portion terminating in a curved distal tip; attaching a pin to the core wire intermediate portion; forming an outer jacket comprising a proximal portion, a distal portion sized for introduction into a patient's body and terminating at a distal end, a lumen extending there between, and a helical slot extending from an open end at the outer jacket distal end proximally and helically around the outer jacket distal portion; directing the core wire proximal portion proximally into the lumen from the outer jacket distal end until the pin is disposed adjacent the outer jacket distal end; aligning the pin with the open end of the helical slot; sliding the pin proximally along the helical slot, thereby further directing the core wire proximally along the outer jacket; and closing the open end, thereby preventing the pin from being removed from the helical slot, while allowing the pin to slide along the helical slot when the core wire is directed axially relative to the outer jacket to rotate the core wire distal tip.

In accordance with yet another embodiment, a system is provided for performing a thrombectomy procedure that includes an elongate tubular member comprising a proximal end, a distal end sized for introduction into a patient's vasculature, and an aspiration lumen extending there between; and a guidewire. The guidewire may include an outer jacket comprising a proximal portion, a distal portion sized for introduction into the aspiration lumen, a lumen extending there between, and one or more helical slots on the distal portion; and an inner core wire comprising a proximal portion and a distal portion, the core wire movably disposed within the lumen of the outer jacket such that the core wire distal portion extends from the outer jacket distal portion, the core wire distal portion terminating in a curved distal tip, the core wire comprising one or more pins adjacent the core wire distal portion, each pin slidably received in a respective helical slot in the outer jacket such that axial movement of the core wire relative to the outer jacket causes the pin to slide within the helical slot and rotate the distal tip relative to the outer jacket distal portion.

In accordance with still another embodiment, a method is provided for accessing a branch body lumen from a main body lumen to perform a procedure within a patient's body that includes providing a guidewire comprising an outer jacket including proximal and distal ends, and a core wire including a distal portion extending from the outer jacket distal end and terminating in a curved distal tip; introducing the guidewire into the main body lumen such that the distal portion is disposed within the main body lumen beyond the outer jacket distal end; directing the core wire axially relative to the outer jacket, thereby causing cooperating elements on the core wire and outer jacket to rotate the distal tip within the main body lumen until the distal tip is oriented towards the branch body lumen; and advancing the entire guidewire to direct the distal tip and distal portion of the core wire into the branch body lumen.

In accordance with yet another embodiment, a method is provided for performing a thrombectomy procedure within a patient's body that includes providing a guidewire comprising an outer jacket including proximal and distal ends, and a core wire including a distal portion extending from the outer jacket distal end and terminating in a curved distal tip; introducing the guidewire into the main body lumen such that the distal portion is disposed within a blood vessel adjacent a clot; advancing the guidewire such a distal tip of the guidewire is introduced at least partially into the clot; and directing the core wire axially relative to the outer jacket, thereby causing cooperating elements on the core wire and outer jacket to rotate the distal tip to at least partially break up the clot.

Other aspects and features including the need for and use of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments. The drawings illustrate exemplary embodiments, in which:

FIG. 1 is a side view of an exemplary embodiment of a guidewire including an inner core wire and an outer jacket.

FIG. 2 is a detail of a distal portion of the guidewire of FIG. 1.

FIGS. 14 and 15 show an exemplary method for making an outer jacket of a guidewire.

FIGS. 16 and 17 show an exemplary method for assembling a guidewire from the core wire of FIGS. 12 and 13 and the outer jacket of FIGS. 14 and 15.

FIG. 18 is a detail of an alternative embodiment of an outer jacket of a guidewire.

FIGS. 19-21 show an exemplary method for assembling a guidewire from the core wire of FIGS. 12 and 13 and the outer jacket of FIG. 18.

DETAILED DESCRIPTION OF THE EXEMPLARY EMBODIMENTS

Figure 3:
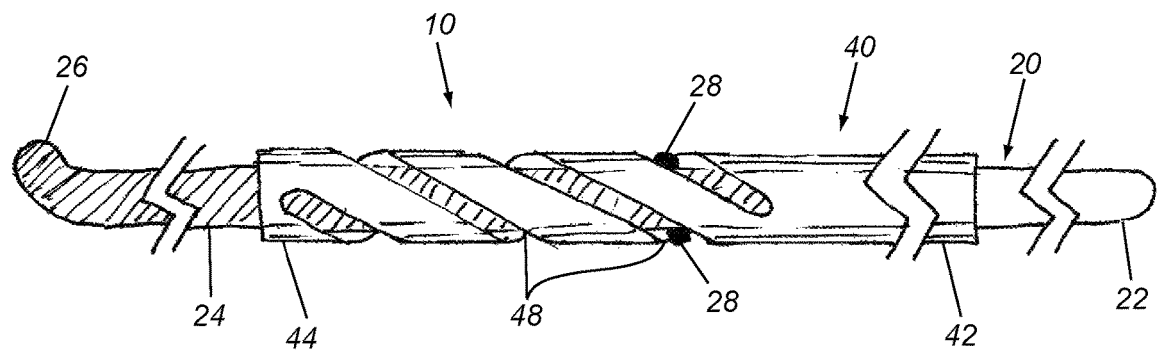
FIGS. 3-5 shows the distal portion of the guidewire of FIGS. 1 and 2, showing the core wire advanced to different positions to rotate and/or advance a distal tip from the outer jacket.
Figure 4:
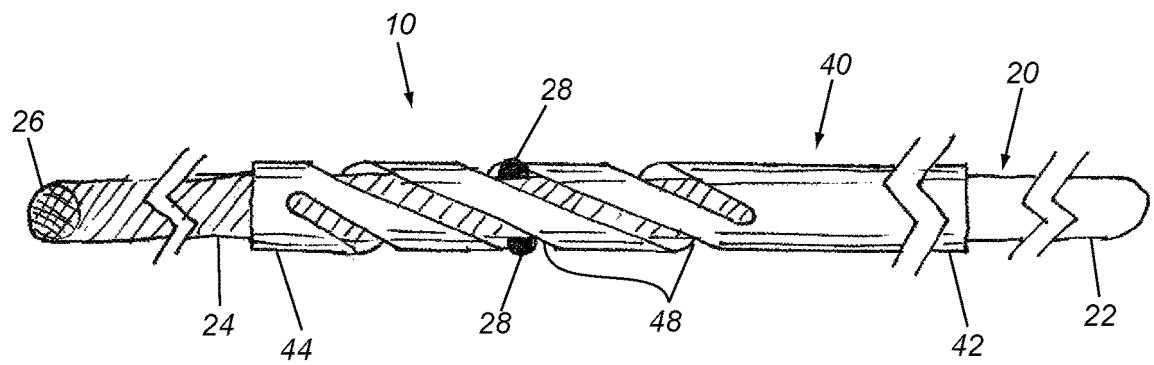
Figure 5:
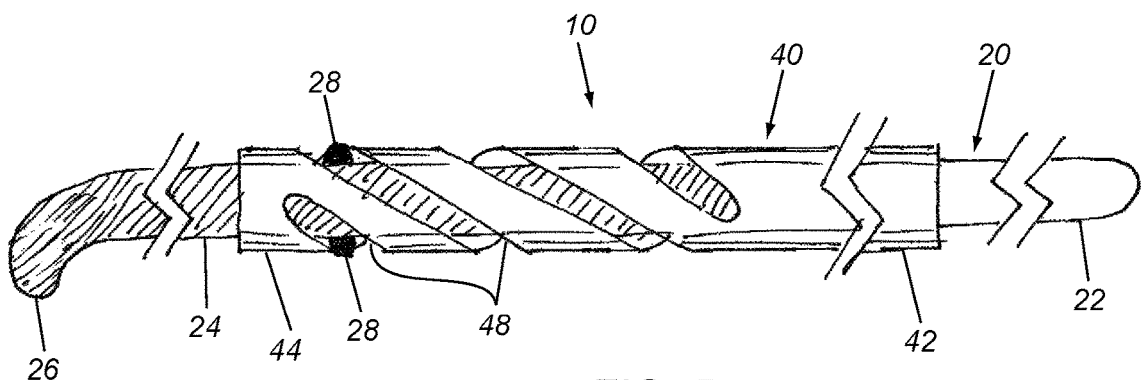

Turning to the drawings, FIGS. 1 and 2 show an exemplary embodiment of a guidewire 10 that includes a proximal end 12, a distal end 14 sized for introduction into a patient's body, and a longitudinal axis 16 extending there between. The guidewire 10 generally includes two components that are movable relative to one another, namely an inner core wire 20 that slides axially and/or rotationally inside an outer jacket 40. As described further elsewhere herein, the outer jacket 40 includes one or more helical slots 48 and the core wire 20 includes one or more corresponding pins 28 that are slidably received within the helical slot(s) 48 such that axial movement (or rotation) of the core wire 20 relative to the outer jacket (3) causes a distal tip 26 of the core wire 20 to rotate and/or be directed axially relative to the outer jacket 40, e.g., as shown in FIGS. 3-5. This therefore requires that the outer diameter of the core wire 20 be slightly smaller than the inner diameter of the outer jacket 40.

Figure 27:
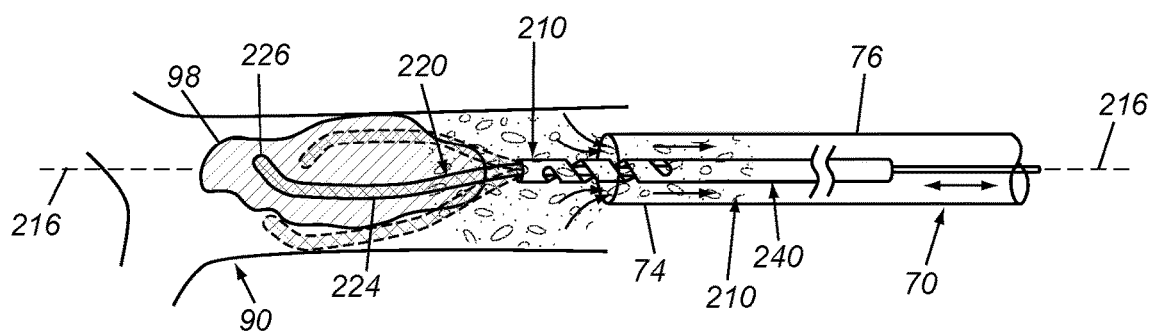
FIG. 27 is a detail of the vessel shown in FIG. 26, showing a distal tip of the guidewire being rotated (in phantom) to break up the clot.

Generally, the core wire 20 includes a proximal portion 22, a distal portion 24 terminating in a distal tip 26 having a desired shape, e.g., a curved or "J" shape, a floppy tip, and/or other atraumatic tip, and one or more pins 28 extending radially from the distal portion 24. Optionally, the distal portion 24 of the core wire 20 may be biased to a predetermined shape, e.g., a substantially straight, curved, or curvilinear shape such that, as the distal portion 24 is advanced from the outer jacket 40, the distal portion 24 may be biased to a desired shape, which may facilitate advancing the distal tip 26 into a branch or other body lumen within a patient's body (not shown). For example, as shown in FIG. 27, a guidewire 210 may be provided that includes a distal portion 224 that is biased to a curved shape, e.g., extending transversely from a longitudinal axis 216 of the guidewire 224 and/or curving to cross the longitudinal axis 216 adjacent the distal tip 226. Alternatively, the distal portion may be biased to a curvilinear shape yet may be manually reshaped by the user, e.g., by adjusting the extent that the distal portion is exposed from the outer jacket or otherwise from the proximal end of the guidewire.

Similarly, the outer jacket 40 includes a proximal end 42, a distal end 44 sized for introduction into a patient's body, and a distal portion 46 including the helical slot(s) 48. In addition, the outer jacket 40 has a lumen 50 extending between the proximal and distal ends 42, 44 sized to slidably receive the core wire 20. In the exemplary embodiment shown, the core wire 20 includes a pair of pins 28 offset proximally from the distal tip 26 by a predetermined distance and extending from opposite sides of the distal portion 24, e.g., defining a transverse axis 29, which may be substantially perpendicular to the longitudinal axis 16, and the outer jacket 40 includes a pair of helical slots 48 offset about one hundred eighty degrees (180°) from one another around the circumference of the outer jacket 40. Although two pins 28 and slots 48 are shown, it will be appreciated that one or more pins and/or slots may be provided as desired, e.g., one pin slidable in a single slot or three or more pins and corresponding slots.

As the core wire 20 is directed axially, e.g., advanced forward, with respect to the outer jacket 40, the pins 28 travel along the path in the helical slots 48 and thereby proportionally rotate or turn the distal tip 26 of the core wire 20. This therefore requires the diameter (or other cross-section) of the pins 28 to be slightly smaller than the width of the helical slots 48.

The helical slot(s) 48 may extend helically around the circumference of the outer jacket 40 for a desired distance, e.g., at least one full turn, i.e., three hundred sixty degrees (360°), as shown in FIGS. 3-5. Alternatively, the helical slot(s) 48 may extend less than a full turn, e.g., a half turn (about one hundred eighty degrees (180°)), or more than a full turn, e.g., two, three, or more turns, if desired. In the example shown in FIGS. 3-5, the distal tip 26 of the core wire 20 may be rotated up to three hundred sixty degrees (360°) relative to the outer jacket 40. For example, FIG. 3 shows the distal tip 26 rotated from a proximal-most position (not shown, e.g., where the distal tip 26 points to the left) about ninety degrees (90°), e.g., such that the distal tip 26 points upwardly. FIG. 4 shows the distal tip 26 rotated about one hundred eighty (180°), e.g., such that the distal tip 26 points to the right. Finally, FIG. 5 shows the distal tip 26 rotated about two hundred seventy (270°), e.g., such that the distal tip 26 points downwardly, i.e., to a distal-most position.

The distance that the core wire 20 must be directed axially to correspond to a desired rotation of the distal tip 26 may correspond to the take-off angle Θ of the helical slots 48 (shown in FIG. 11), e.g., as described elsewhere herein. For example, if the take-off angle Θ is relatively large, e.g., greater than forty five degrees (45°), the distal tip 26 may be rotated with minimal axial movement of the core wire 20, while if the take-off angle is relatively small, e.g., approaching five degrees (5°), the core wire 20 must be moved further axially in order to achieve the same rotation.

The proximal end 22 of the core wire 20 may extend from the proximal end 42 of the outer jacket 40 sufficient distance to facilitate holding and manipulating the core wire 20 relative to the outer jacket 40. Optionally, the proximal end 22 of the core wire 20 may include one or more visual markers (not shown) that may be aligned with the proximal end 42 of the outer jacket 40 (or other feature, not shown on the proximal end 42) to identify the rotational position of the distal tip 26 relative to the distal end 44 of the outer jacket 40. In another option, the distal tip 26 and/or the distal end 44 may include one or more markers to facilitate identification and/or orientation of the distal tip 26 within a patient's body using external imaging, e.g., one or more radiopaque markers that may be identified using fluoroscopy. Alternatively, the distal tip 26 and/or the entire distal portion 24 of the core wire 20 may be constructed using platinum or other radiopaque material, which may facilitate visualizing the guidewire 10 under the fluoroscopy.

Optionally, the location of the distal portion 46 of the outer jacket 40 (i.e., having the helical slot(s) 48) with respect to the distal tip 26 of the core wire 20 may be varied depending upon the intended vasculature in which the guidewire 10 to be used. In addition or alternatively, the axial length HL (shown in FIG. 11) of the helical slot(s) 48 may be varied to provide a desired minimum exposed length and/or maximum exposed length of the core wire 20.

Figure 6:
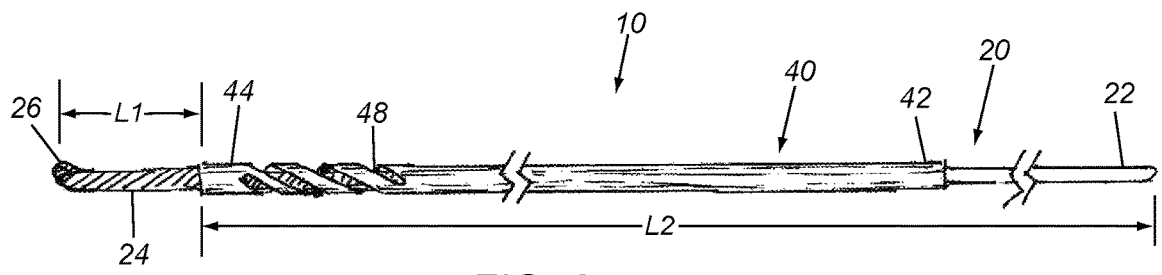
FIGS. 6-8 are side views of alternative embodiments of guidewires having a distal tip of an inner core wire located different distances from an outer jacket of the guidewires.
Figure 7:
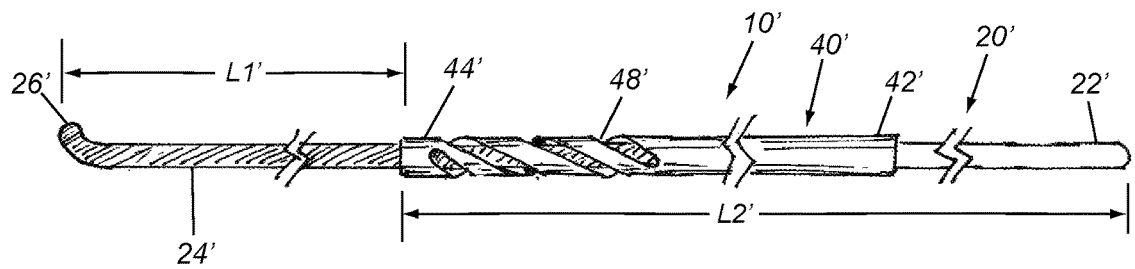
Figure 8:
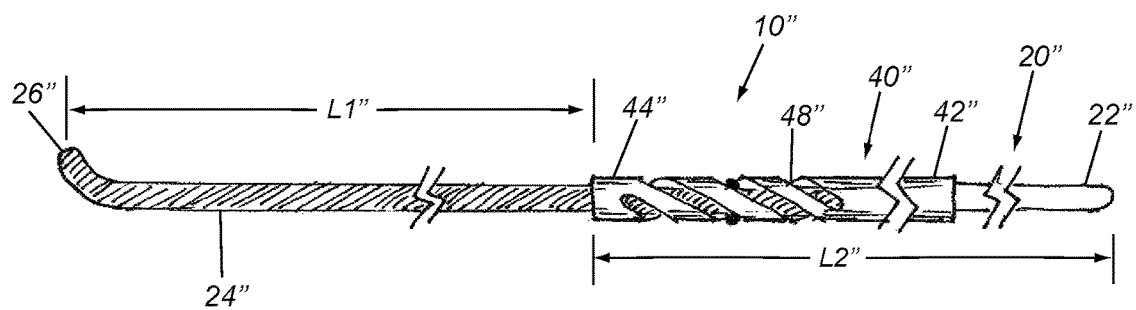

For example, FIGS. 6-8 show alternative embodiments where the outer jackets 40-40" have similar axial lengths and take-off angles for the helical slot(s) 48-48" and different lengths of distal portions 24-24" of the core wires 20-20" beyond the distal end 44-44" of the outer jackets 40-40." For example, for the guidewire 10 shown in FIG. 6, when the core wire 20 is advanced from its proximal-most position to its distal-most position relative to the outer jacket 40, a desired length L1 of the core wire 20 may be exposed from the distal end 44 of the outer jacket 40, e.g., between about five and ten centimeters (5-10). In this embodiment, the length L2 of the guidewire 10 from the distal end 44 of the outer jacket 40 to the proximal end 22 of the core wire 20 may be between about 180-200 centimeters.

By comparison, FIG. 7 shows an exemplary guidewire 10' in which the exposed length L1' of the core wire 20' (between the distal end 44' of the outer jacket 40' and the distal tip 26') may be between about fifteen and twenty centimeters (15-20 cm), and the length L2' may be between about 160-180 centimeters. Finally, FIG. 8 shows an exemplary guidewire 10" in which the exposed length L1" of the core wire 20" may be between about forty and fifty centimeters (40-50 cm), and the length L2" may be between about 140-150 centimeters.

Figure 9:
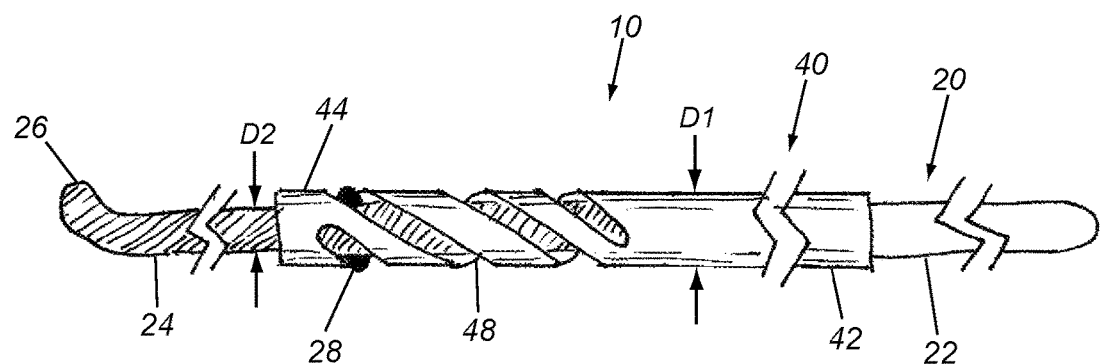
FIGS. 9-11 are details of the guidewire of FIG. 1, showing exemplary dimensions for components of the guidewire.
Figure 10:
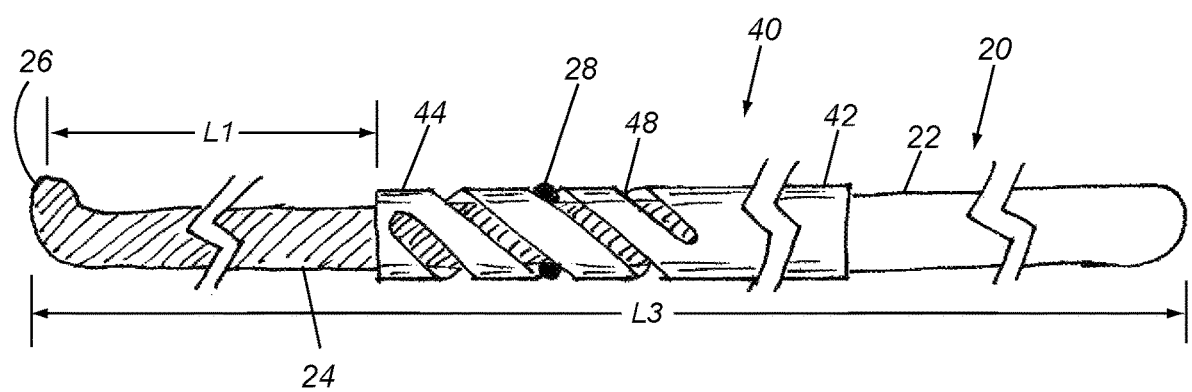
Figure 11:
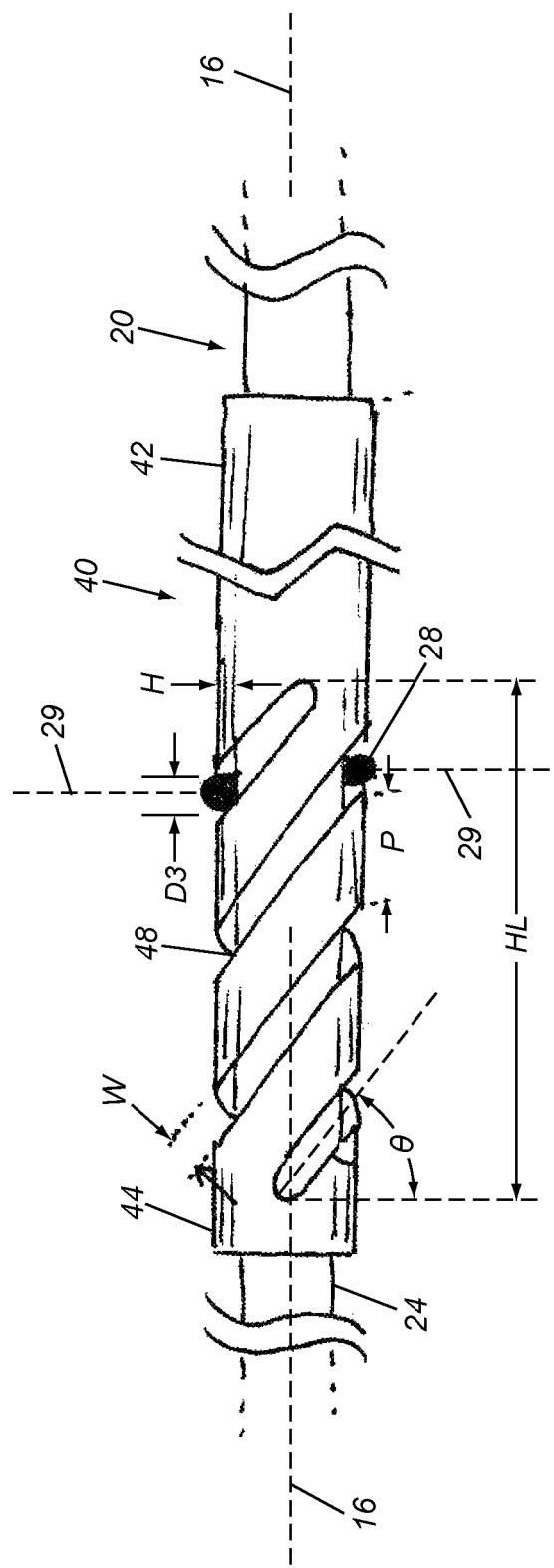

In general, a guidewire of any size can be manufactured using the systems and methods herein. FIGS. 9-11 show exemplary dimensions that may be provided for a guidewire made according to the systems and methods described herein. For example, for neurovascular applications, the guidewire 10 of FIG. 1 may have an outer diameter between about 0.010 inch to 0.050 inch (0.25-1.25 mm), e.g., to accommodate one or more catheters or other tubular devices (not shown) being advanced over the guidewire 10 during a procedure. To manufacture such a guidewire 10, as shown in FIG. 9, the outer jacket 40 should have an outer diameter D1 between about 0.010 inch to 0.050 inch (0.25-1.25 mm), e.g., substantially uniformly along its length and/or without any abrupt transitions that may impair movement of a tubular device over the guidewire 10. The inner core wire 20 would have an outer diameter slightly smaller than the inner diameter of the lumen 50 of the outer jacket 40 in order to be slidably received therein. In an exemplary embodiment, the core wire 20 may have an outer diameter D2 between about 0.004 inch to 0.045 inch (0.1-0.9 mm).

In other applications, e.g., involving a patient's peripheral and/or cardio-vasculature, the guidewire 10 and its components may have larger diameters. Thus, the systems and methods herein may be scalable to manufacture guidewires with outer diameters beyond the range of 0.010 inch to 0.050 inch (0.25-1.25 mm), e.g., where the size of catheters delivered over the guidewires may be typically larger, e.g., greater than about 0.050 inch (1.25 mm). For example, the outer jacket 40 may have an outer diameter D1 between about 1.25-2.00 mm, while the core wire 20 may have an outer diameter D1 between about 1.00-1.90 mm for such applications.

In addition or alternatively, as shown in FIG. 10, the overall length L3 of the guidewire 10 may be varied depending on the application and/or distance from the access site to the region of the patient's body where the procedure is to be performed. For example, the core wire 20, which defines the overall length of the guidewire 10 may have a length L3 between about one hundred and three hundred centimeters (100-300 cm). In addition, as described elsewhere herein, the distance L1 from the distal end 44 of the outer jacket (i.e., the distal-most end of the helical slots 48) may be between about five and one hundred centimeters (5-100 cm), again depending on the application and/or region being accessed. It will be appreciated that the ability to torque the distal tip 26 of the guidewire 10 generally decreases as the distance L1 increases. Therefore, for applications where it is desired to more directly torque the distal tip 26, the distance L1 may be reduced.

In addition or alternatively, as shown in FIG. 11, the dimensions of the helical slots 48 may be varied, as desired, e.g., to control the degree of axial movement of the core wire 20 to cause desired rotation of the distal tip 26 and/or to control the minimum and maximum exposed length of the core wire 20. In an exemplary embodiment, the helical slots 48 in the outer jacket 40 may define a take-off angle Θ relative to the longitudinal axis 16 that may be between about five and seventy five degrees (5-75°). The axial spacing or pitch P between adjacent helical slot(s) 48 may vary, for example, between about 0.002 inch and 0.100 inch (0.05-2.5 mm). The number of turns of the helical slot(s) 48 may also vary, for example, from less than one (1) turn to up to five (5) turns.

Based on the take-off angle Θ and the number of turns, the helical slot(s) 48 may have an axial length HL that may correspond to the length of the core wire 20 that may be advanced from and retracted into the outer jacket 40 while rotating the distal tip 26. In an exemplary embodiment, the axial length HL of the helical slot(s) 48 may be between about five and thirty millimeters (5-30 mm). Optionally, if the axial length HL is relatively long, the helical slot(s) 48 may be offset a predetermined distance from the distal end 44 of the outer jacket 40. For example, a relatively long distal portion 46 may increase the stiffness of the resulting guidewire 10, and so it may be desirable to offset the helical slot(s) 48 proximally from the distal end 44 of the outer jacket 40 and/or from the distal tip 26, e.g., to increase the flexibility of the guidewire portion beyond the helical slot(s) 48.

In addition, the number of parallel helical slots 48, i.e., offset from one another around the circumference of the outer jacket 40 may be varied, as desired, e.g., from one to four (1-4) slots 48. However, it will be appreciated that two helical slots offset from one another about one hundred eighty degrees (180°) around the circumference from one another may be adequate for most systems. Such symmetry may prevent rotation of the core wire 20 from applying undesired bending or other forces to the outer jacket 40.

In addition, the helical slots 48 may have a width W, e.g., when machined, laser-cut, or otherwise formed in the outer jacket 40 between about 0.002 inch and 0.100 inch (0.05-2.5 mm). The corresponding pins 28 on the core wire 20 should have a diameter (or other cross-sectional dimension) slightly smaller than the width W of the helical slots 48, e.g., to allow the pins 28 to slide freely along the helical slots 48 as the core wire 20 is directed axially (or rotated). For example, the pins 28 may have a cylindrical shape defining a diameter D3 (relative to the transverse axis 29) that is smaller than the width W, e.g., between about 0.001 inch and 0.098 inch (0.025-2.45 mm). In addition, the side walls of the pins 28 should be substantially smooth to reduce friction with the walls of the helical slots 48.

In addition, the pins 28 may have a height H such that the pins 28 may slidably engage the walls of the helical slots 48 without catching or otherwise introducing undesired friction or resistance to movement. In one embodiment, the height H may be such that the outer tips of the pins 28 do not extend above the outer surface D1 of the outer jacket 40 (or otherwise exceed the outer diameter D1 of the guidewire 10 shown in FIG. 9). The tips of the pins 28 may be rounded or otherwise formed, e.g., to avoid any sharp edges that may contact tissue adjacent the guidewire 10. In an alternative embodiment, the helical slots 48 may be formed as grooves on an inner surface of the outer jacket 40 without extending to the outer surface (not shown), and the pins 28 may have a corresponding height to be slidably received in the grooves.

Turning to FIGS. 12-17, an exemplary method is shown for making a guidewire 110 that includes a central wire 120 and an outer jacket 140. While there may be multiple ways to manufacture and assemble such a guidewire 110, exemplary materials and methods for manufacturing and/or assembling the guidewire 110 will now be described. Generally, the guidewire 110 may be made by first manufacturing individual components for the central wire 120 and outer jacket 140, and then assembling the components together to form the finished guidewire 110.

For example, the inner core wire 120 may be made from typical guidewire material, e.g., stainless steel and/or other metal. The core wire 120 may be integrally formed as a single piece or may be formed as multiple pieces that are assembled together part. For example, the core wire 120 may include a central wire surrounded by a coiled wire (not shown), e.g., both extending substantially the entire length of the core wire 120. The central wire may be fixed relative to the coiled wire, e.g., by interference fit, bonding with adhesive, welding, and the like, thereby provide a flexible core wire 120 that is resistant to kinking and/or transfers torsional forces from the proximal portion 122 to the distal portion 124. Alternatively, the core wire 120 may be formed as a single solid or hollow wire. Optionally, the outer surface of the core wire 120 may be coated, e.g., with a lubricious material, to provide a desired finish, e.g., to facilitate axial movement of the core wire 120 within the outer jacket 140.

The distal tip 126 may be heat treated and/or otherwise processed to set a desired shape, e.g., a "J" tip and/or other curved shape in the distal tip 126. Alternatively, the distal tip 126 may be formed separately (not shown) and attached to a distal end of a straight section of wire.

The pins 128 may be formed from any biocompatible material such as stainless steel, titanium, Nitinol or other nickel (Ni) alloy, cobalt-chrome (Co—Cr) alloy, extruded or unextruded polymer, PEEK material, solder material, hard glue material, and the like. In one embodiment, e.g., as shown in FIGS. 1 and 2, separate pins 28 may be attached to the outer surface of a core wire 20, e.g., at a predetermined location offset from the distal tip 26. For example, tabs may be formed directly on the core wire 20, e.g., by molding and the like, or may be formed separately and then attached to the core wire 20, e.g., by bonding with adhesive, welding, soldering, and the like.

Alternatively, in the embodiment shown in FIGS. 12-13 and 16-17, a single pin member 128a may be provided that may be inserted through a hole 136 formed in the core wire 120 to provide a pair of opposite pins 128. The pin member 128a may be attached to the core wire 120, e.g., by interference fit, bonding with adhesive, welding, soldering, and the like, thereby fixing the pins 128 to define the transverse axis 129.

Figure 12:
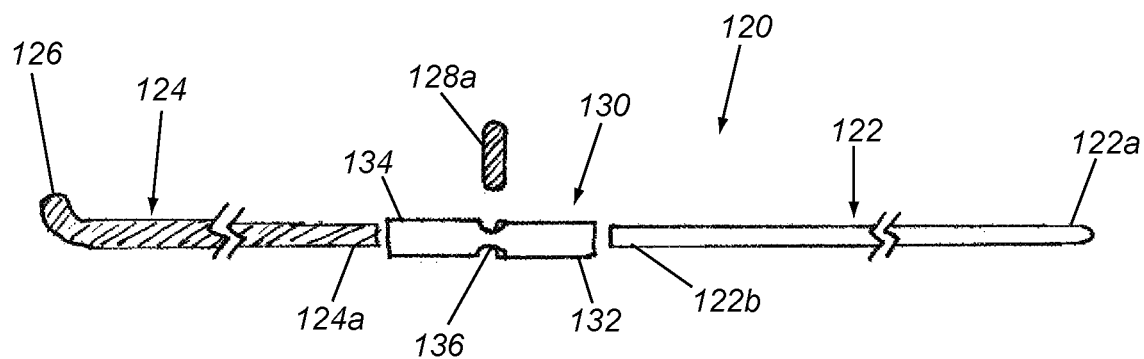
FIGS. 12 and 13 show an exemplary method for making a core wire of a guidewire.
Figure 13:
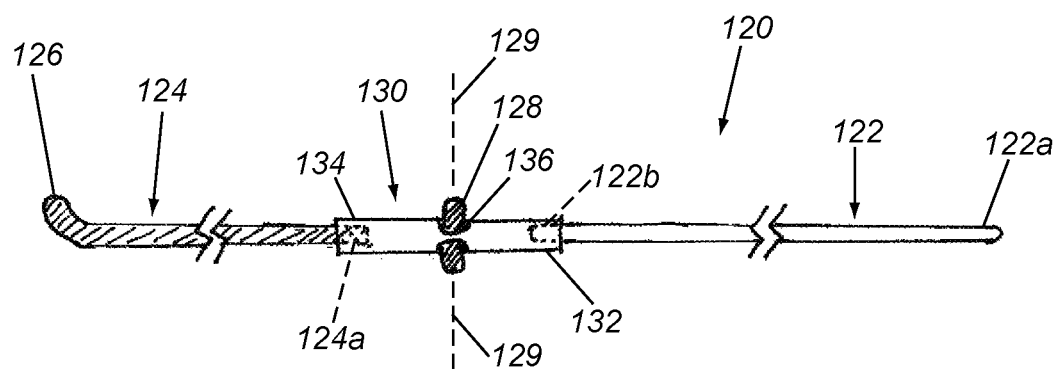

With particular reference to FIGS. 12 and 13, an exemplary embodiment of a core wire 120 is shown that includes three components attached together, namely a proximal portion 122, a distal portion 124, and an intermediate cylindrical portion 130 there between. In an exemplary embodiment, the distal portion 124 may be manufactured using conventional methods and materials, e.g., a metallic coil wound over a central wire. The distal portion 124 may have a substantially uniform diameter along its length, e.g., from its proximal end 124a to the distal tip 126, smaller than the lumen 50 of the outer jacket 40 (not shown, see FIGS. 16 and 17).

Similarly, the proximal portion 122 may also be formed as a metallic coil wound over a central wire having sufficient length to extend to the proximal end 122a of the core wire 120. Alternatively, the proximal portion 122 may be a single solid or hollow wire. The proximal portion 122 may have a substantially uniform diameter along its length. Alternatively, the diameter of the proximal portion 122 may vary along its length, e.g., by grinding, machining, molding, extruding, casting, and the like, to profile of multiple diameters to achieve the desired stiffness/flexibility for the application. For example, a region of the proximal portion 122 that is not received in the outer jacket 140 may have a relatively larger diameter, e.g., similar to the outer jacket 140, since the proximal portion 122 may only be introduced into relatively larger body lumens, which may enhance pushability of the core wire 120 and/or transfer of torque from the proximal end 122 to the distal tip 126.

The intermediate portion 130 may be a relatively short tubular body having proximal and distal ends 132, 134 and a through hole 136 machined, drilled, or otherwise formed therethrough. The tubular body may be formed from metal, e.g., stainless steel, plastic, composite materials, and the like. In an exemplary embodiment, the intermediate portion 130 may have a length of ten millimeters (10 mm) or less, and the through hole 136 may be located in the center of the intermediate portion 130, i.e., spaced substantially equally from the proximal and distal ends 132, 134.

To assemble the core wire 120, the distal end 122b of the proximal portion 122 may be inserted into and/or otherwise attached to the proximal end 132 of the intermediate portion 130. For example, the proximal end 132 may include a recess sized to receive the distal end 122b. Similarly, the proximal end 124a of the distal portion 124 may also be inserted into and/or otherwise attached to the distal end 134 of the intermediate portion 130. The proximal and distal portions 122, 124 may be substantially permanently attached to the intermediate portion 130, e.g., by one or more of interference fit, threads, detents, or other cooperating connectors (not shown), welding, soldering, bonding with adhesive, e.g., UV-cured glue, polymer heat shrink, and the like.

The through hole 136 may be sized to receive a pin member 128a, which may be formed from materials similar to other components herein, e.g., metal, such as stainless steel, plastic, composite materials, and the like. As shown in FIGS. 12, 13, 16, and 17, the pin member 128a may be inserted through the hole 136 to define opposite pins 128, e.g., during assembly of the guidewire 10, as described further below. Optionally, one or more of the intermediate portion 130, distal portion 124, and/or pin member 128a may be formed from metal or other material that may be chemically polished, coated, and/or otherwise treated (either before or after assembly) to provide a desired finish for the outer surface of the core wire 120, e.g., to reduce friction and/or facilitate movement of the core wire 120 relative to the outer jacket 140.

Similar to the core wire 120, the outer jacket 140 may be integrally formed as a single piece or more be formed from multiple pieces that are assembled together. In the exemplary embodiment shown in FIGS. 1 and 2, the outer jacket 40 may be formed from a single length, e.g., of extruded or unextruded polymer tubing material, helical wire, and the like, with the helical slot(s) 48 machined, laser-cut, or otherwise formed through the wall.

Alternatively, as shown in FIGS. 14 and 15, an outer jacket 140 may be provided that includes a relatively long proximal portion 152 and a relatively short distal portion 146, e.g., tubular body 154 (having the helical slot(s) 148) that are attached together.

For example, the distal portion 146 may be formed from a length of hypotube 154 and the proximal section 152 may be formed from a length of tubing material, helical wire, and the like. The hypotube 154 may be formed from a variety of materials, such as stainless steel, titanium, Nitinol or other nickel (Ni) alloy, cobalt-chrome (Co—Cr) alloy, extruded or unextruded polymer, PEEK material, and the like. The hypotube 154 may have sufficient length between its proximal and distal ends 154a, 154b to accommodate the helical slot(s) 148 being machined, laser-cut, or otherwise formed through its wall. The proximal end 154a of the hypotube 154 may be attached to a distal end 152b of the proximal section 152 using one or more of interference fit, one or more threads, tabs, or other cooperating connectors (not shown), solder, glue, polymer heat shrink, and the like.

In an exemplary embodiment, the hypotube 154 may be formed from a stainless steel cylinder having an inner diameter sized to slidably receive the intermediate portion 130 of the core wire 120 and including a pair of helical slots 148 machined or otherwise formed through the side wall of the hypotube 154. The proximal portion 152 may be formed from polymeric tubing (e.g., extruded or assembled polymeric tubing) having a length that is slightly less than the length of the proximal portion 122 of the core wire 120, e.g., such that the proximal end 122a extends out of a proximal end 152a of the proximal portion 152 of the outer jacket 140 to allow actuation from the proximal end 122a of the guidewire 110, similar to other embodiments herein. During assembly of the outer jacket 140, the proximal end 154a of the hypotube 154 may be inserted partially into the distal end 152b of the proximal portion 152, e.g., as shown in FIG. 15, and/or the components may be substantially permanently attached together, e.g., by one or more of polymeric heat shrink, bonding with adhesive (e.g., glue/UV glue), sonic welding, and the like.

Turning to FIGS. 16 and 17, the guidewire 110 may be assembled once the core wire 120 and outer jacket 140 are fabricated. During final assembly, the previously-assembled core wire 120 may be inserted into the previously-assembled outer jacket 40, e.g., until the hole 136 aligns with slots 148 as shown in FIG. 17. The pin member 128a may then be inserted through the slots 148 and into the hole 136 such that the ends of the pin member 128a extend transversely from opposite sides of the intermediate portion 130. Once fully inserted, the ends providing the pins 128 may remain substantially flush with the outer surface of the hypotube 154 or may extend slightly radially outwardly relative to the outer surface. The pin member 128a may be secured relative to the hole 136, e.g., by one or more of interference fit, bonding with adhesive, and the like, to prevent the core wire 120 from being removed entirely from the outer jacket 140, while allowing the core wire 120 to be moved axially, thereby causing the pins 128 to slide helically along the helical slots 148 and rotate the distal tip 126 of the core wire 120, similar to other embodiments herein.

Turning to FIGS. 18-21, an alternative embodiment of a guidewire 110' is shown that includes a core wire 120, similar to that shown in FIGS. 12 and 13, and a variation of an outer jacket 140' best seen in FIG. 18. Similar to previous embodiments, the outer jacket 140' includes a relatively long proximal portion 152' and a distal portion 154' including one or more helical slots 148,' generally similar to previous embodiments. As shown, the proximal and distal portions 152,' 154' are integrally formed from a single section of tubing, e.g., into which the helical slot(s) 148' are machined, laser-cut, or otherwise formed. Alternatively, the proximal and distal portions 152,' 154' may be formed separately and attached together, e.g., similar to the outer jacket 140 shown in FIGS. 14 and 15.

Unlike the previous embodiments, the helical slot(s) 148' (two shown) include an open distal end 148a' at the distal end 144' of the outer jacket 140' and the helical slot(s) 148' extend helically and proximally from the open end 148a' to a closed proximal end 148b.' This configuration of the helical slot(s) 148' may facilitate assembly of the guidewire 110.'

For example, the core wire 120 may be manufactured and assembled similar to the previous embodiments, e.g., as shown in FIGS. 12 and 13. In particular, the pin member 128a may be inserted into the hole 136 in the intermediate portion 130 and attached thereto before the core wire 120 is inserted into the outer jacket 140.'

Figure 21:
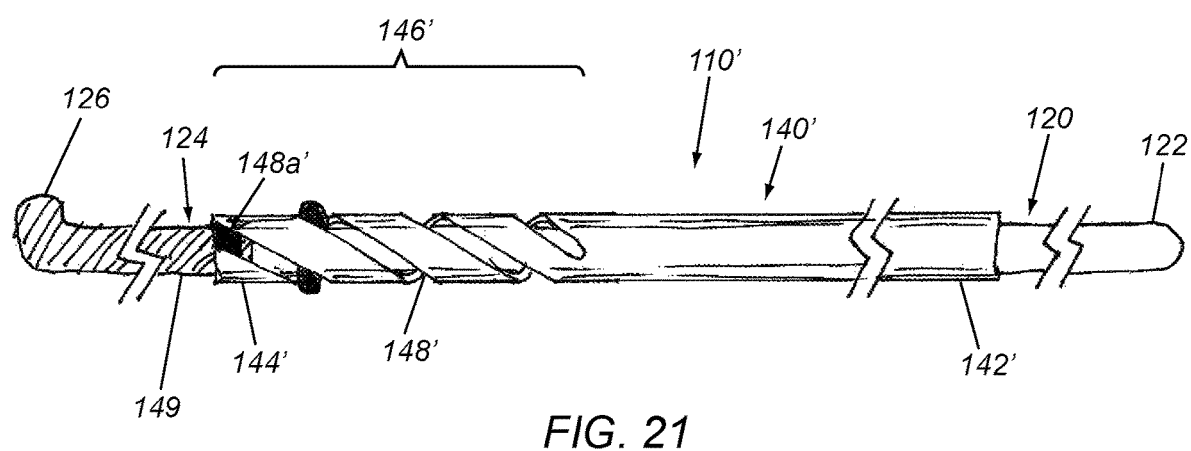

Once the core wire 120 is fully assembled, the proximal end 122a may be inserted into the distal end 144' of the outer jacket 140' into the lumen 150.' For example, as shown in FIG. 19, the pins 128 may be aligned with the open ends 148a' of the helical slots 148' and the core wire 120 may be rotated relative to the outer jacket 140' to slide the pins 128 along the helical slots 148' and advance the core wire 120 further into the lumen 150, as shown in FIG. 20. Once the pins 128 are clear of the open ends 148a,' the open ends 148a' may be closed, as shown in FIG. 21, e.g., by one or more of filling the open ends 148a' with solder, glue, UV glue, or other material, inserting a plug (not shown) over the distal portion 124 of the core wire 120 into the distal end 144' of the outer jacket 140,' applying a heat shrink polymer (not shown) around the distal end 144,' and the like. The core wire 120 may then be freely advanced and retracted as desired, limited by the material closing the open end 148a' (and the closed proximal end 148b'), similar to other embodiments herein.

Figure 24:
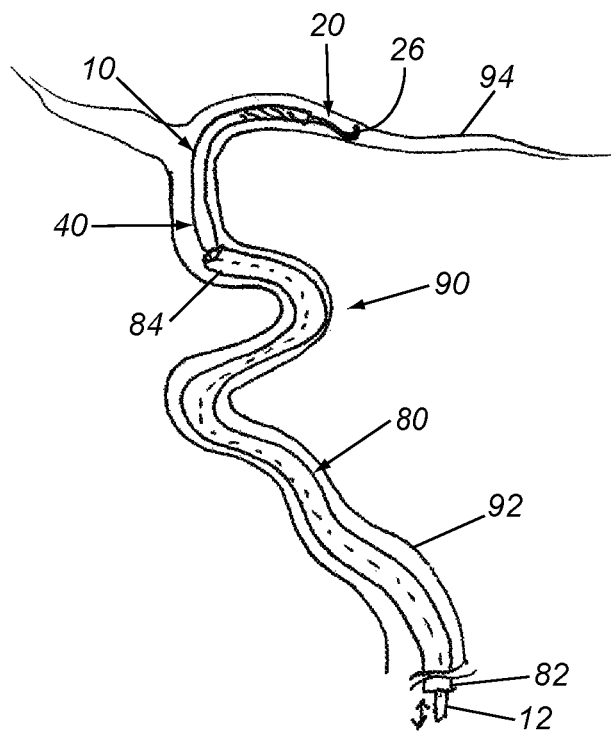
Figure 25:
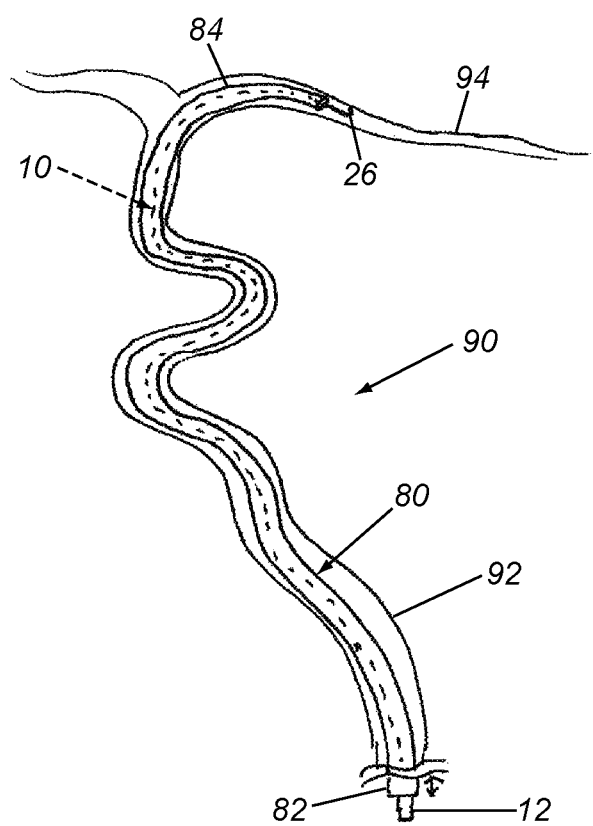

The guidewires herein may be used to perform a variety of medical procedures within a patient's body, e.g., to access blood vessels or other body lumens within the patient's body and/or facilitate introducing one or more catheters, sheaths, or other devices over the guidewire. For example, FIGS. 23-25 show an exemplary method for accessing a target vessel 94 within a patient's vasculature 90 using a guidewire 10 (which may be any of the embodiments herein) to direct a catheter 80 into the target vessel 94.

Generally, a percutaneous puncture or cut-down may be created at a peripheral location (not shown), such as a femoral artery, carotid artery, or other entry site, and the distal end of the guidewire 10 may be advanced through the patient's vasculature from the entry site, e.g., alone or with the aid of a guide catheter or sheath (not shown). Once positioned with a first vessel, such as main vessel 92 shown in FIG. 22, it may be desirable to access another vessel, such as branch vessel 94, extending from the main vessel 92. In an exemplary embodiment, the main vessel 92 may be an internal carotid artery, and the branch vessel 94 may be a vessel within the patient's neural vasculature, which may be difficult to access given the tortuosity often encountered within the neural vasculature.

Figure 22:
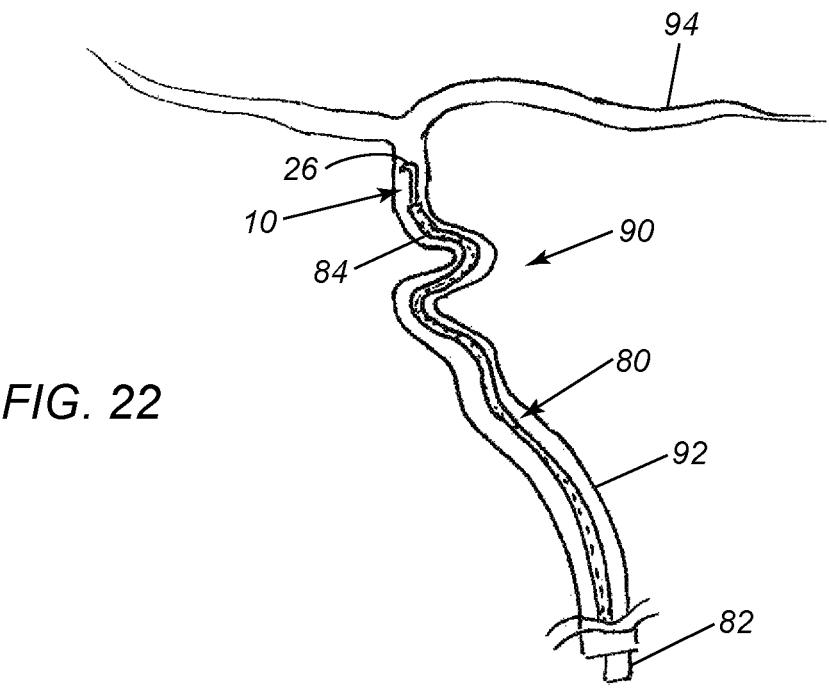
FIGS. 22-25 are cross-sectional views of a patient's vasculature showing a method for delivering a catheter using a guidewire, such as the guidewire of FIG. 1.

As shown in FIG. 22, the distal tip 26 may be disposed within the main vessel 92 proximal to the branch vessel 94, e.g., with the distal end 84 of the catheter 80 disposed proximal to the distal tip 26 (alternatively, the catheter 80 may be introduced after accessing the branch vessel 94). To access the branch vessel, the guidewire 10 may be manipulated from the proximal end 12 (outside the patient's body), e.g., by advancing or otherwise axially moving the core 20 relative to the outer jacket 40 (not shown for clarity), thereby causing the distal tip 26 to rotate within the main vessel 92.

Figure 23:
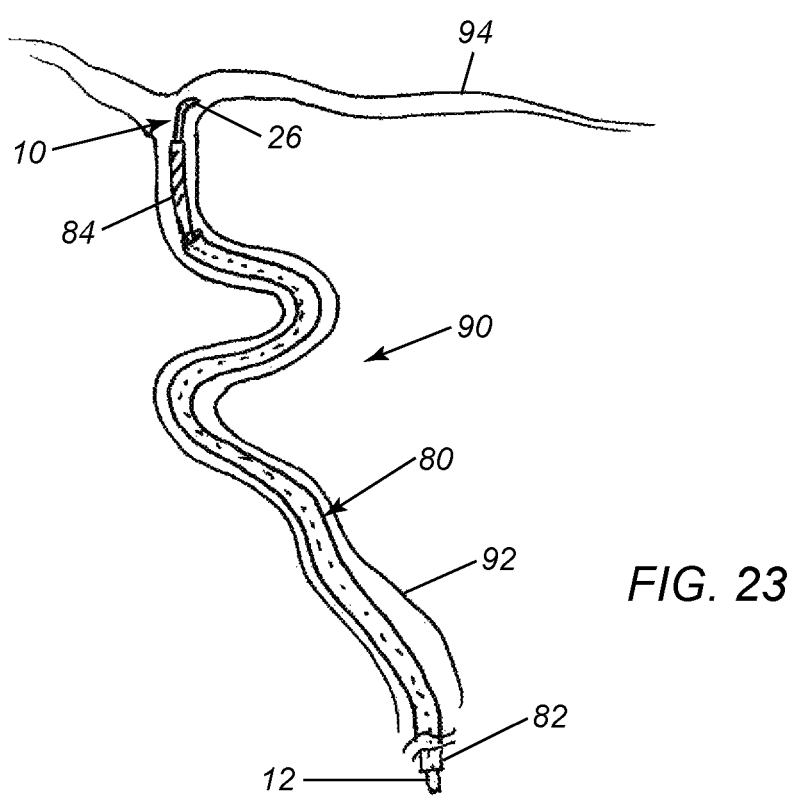

As shown in FIG. 23, the distal tip 26 has been rotated about one hundred eighty degrees (180°) from the position shown in FIG. 22. Fluoroscopy or other external imaging may be used to monitor the position and rotational orientation of the distal tip 26 relative to the branch vessel 94, e.g., to ensure that the distal tip 26 is oriented towards the branch vessel 94, as shown in FIG. 23. Once properly oriented, the entire guidewire 10 may be advanced from the main vessel 92 into the branch vessel 94 (while the distal end 84 of the catheter 80 remains within the main vessel 92), as shown in FIG. 24.

After directing the distal tip 26 sufficiently into the branch vessel 94, the catheter 80 may be advanced over the guidewire 10 to direct the distal end 84 into the branch vessel 94, as shown in FIG. 25. This process may be repeated as often as desired until a target location has been accessed. The catheter 80 may then be used to perform one or more procedures at the target location, e.g., to deliver a stent, embolic coil, and the like (not shown). Optionally, the procedure may involve removing the catheter 80 and advancing one or more additional devices (not shown) over the guidewire 10 or advancing one or more devices through the catheter 80 over the guidewire 10. Once the procedure is completed, the catheter 80 (or other devices) may be removed, and the guidewire 10 may be removed from the patient's body.

Figure 26:
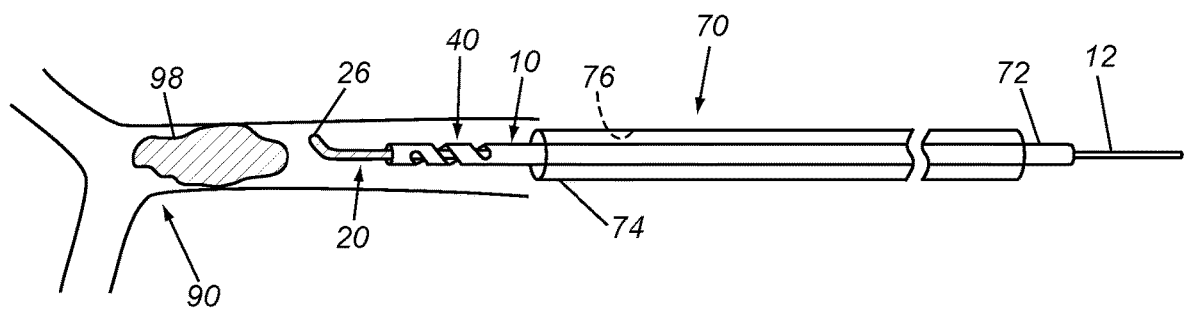
FIG. 26 is a cross-sectional of a patient's vasculature showing a method for treating a blood clot within a vessel using a guidewire, such as the guidewire of FIG. 1.

Turning to FIG. 26, another exemplary method is shown for breaking up and/or removing a blood clot (or other object) 98 within a patient's vasculature 90 (or other body lumen) using a guidewire 10 (which may be any of the embodiments herein). The guidewire 10 may be part of a system 8, e.g., including an aspiration catheter 70. The aspiration catheter 70 generally includes a proximal end 72, a distal end 74 sized for insertion into a patient's body, and an aspiration lumen 76 extending there between. The system may also include one or more additional components, e.g., a source of vacuum or aspiration, e.g., a syringe or vacuum line (not shown) coupled to the proximal end 72 of the aspiration catheter 70 outside the patient's body and communicating with the aspiration lumen 76. In addition, a source of fluid, e.g., to flush the vessel 90 and/or deliver one or more agents to treat the clot 98 may also be coupled to the proximal end 72 and communicating with the lumen 76.

Similar to the previous method, the guidewire 10 may be introduced from an entry site (not shown) into the patient's vasculature 90 until the distal tip 26 is disposed adjacent a target clot 98, as shown in FIG. 26. The distal end 74 of the aspiration catheter 70 may be introduced over the guidewire 10 and advanced through the patient's vasculature 90 until disposed adjacent the distal tip 26. The guidewire 10 may then be advanced and/or otherwise manipulated to advance the distal tip 26 into and/or through the clot 98. The core wire 20 may be advanced relative to the outer jacket 40, thereby causing the distal tip 26 to advance and rotate, e.g., as it is advanced into the clot 98 or after initially advancing the entire guidewire 10 to position the distal tip 26 within the clot 98. The clot 98 may be fragmented by advancing and retracting (back and forth motion) of the core wire 20 through the clot mass. The axial back and forth motion of the core wire 20 enables the distal tip 26 of the core wire 20 to interact with the clot mass and initiate the fragmentation of the clot 98. The source of vacuum may be activated to aspirate the fragmented clot 98 into the lumen 76 of the aspiration catheter 70, e.g., substantially continuously or intermittently, as desired, to remove segments of the clot 98 from the vessel 90.

Optionally, as shown in FIG. 27, the distal portion 224 of the core wire 220 may be biased to a nonlinear, e.g., curved shape, such that the distal portion 224 is offset from a central axis 216 of the guidewire 210 when deployed. Axial movement of the core wire 220 relative to the outer jacket 240 causes the distal portion 224 to rotate within the vessel 90 and/or clot 98, e.g., as shown in phantom in FIG. 27, which may enhance breaking up the clot 98 and/or removing segments of clot material on the wall of the vessel 90. Again, aspiration may be applied to the lumen 76 to remove the segments of the clot 98 into the aspiration catheter 70, as desired. Once the sufficient clot is removed, aspiration may be discontinued, and the catheter 70 and guidewire 10 or 210 may be removed from the patient's body.

In addition or alternatively, the outer surface of the distal portion 24 of the core wire 20 may be modified, e.g., to enhance the wire-clot interaction. For example, the outer surface may be roughened or include one or more features, e.g., bumps, bristles, and the like (not shown), that may enhance fragmentation of the clot 98 while remaining substantially atraumatic to avoid risk of injury to the vessel wall. For example, a plurality of polymeric beads (not shown) may be provided on the outer surface, or a plurality of relatively short segments of polymeric tubing (also not shown) may be attached around the distal portion 24, which may provide additional surfaces and/or edges to enhance engagement with and/or fragmentation of the clot 98.

While the invention is susceptible to various modifications, and alternative forms, specific examples thereof have been shown in the drawings and are herein described in detail. It should be understood that the invention is not to be limited to the particular forms or methods disclosed, but to the contrary, the invention is to cover all modifications, equivalents and alternatives falling within the scope of the appended claims.

I claim:

1. A system for performing a thrombectomy procedure, comprising:

an elongate tubular member comprising a proximal end, a distal end sized for introduction into a patient's vasculature, and an aspiration lumen extending there between; and a guidewire comprising:

an outer jacket comprising a proximal portion, a distal portion sized for introduction into the aspiration lumen, a lumen extending there between, and one or more helical slots on the distal portion; and an inner core wire comprising a proximal portion and a distal portion, the core wire movably disposed within the lumen of the outer jacket such that the core wire distal portion extends from the outer jacket distal portion, the core wire distal portion terminating in a curved distal tip, the core wire comprising one or more pins adjacent the core wire distal portion, each pin slidably received in a respective helical slot in the outer jacket such that axial movement of the core wire relative to the outer jacket causes the pin to slide within the helical slot and rotate the distal tip relative to the outer jacket distal portion.

2. The system of claim 1, wherein the core wire distal portion is biased to a curved shape when deployed within a body lumen, and wherein the core wire distal portion is configured to rotate about a central axis of the outer jacket when the core wire is directed axially relative to the outer jacket.

3. The system of claim 1, further comprising a source of vacuum coupled to the proximal end of the tubular member and communicating with the aspiration lumen for aspirating clot into the aspiration lumen.

4. The system of claim 1, wherein the outer jacket includes two helical slots offset from one another around a circumference of the outer jacket, and the core wire includes two corresponding pins.

5. The system of claim 4, wherein the pins extend from opposite sides of the core wire distal portion such that pins define a transverse axis substantially perpendicular to the longitudinal axis.

6. The system of claim 4, the core wire further comprising a hole extending through the core wire distal portion and a pin member inserted through the hole, the ends of the pin member defining the two pins.

7. The system of claim 1, wherein the outer jacket has a maximum outer diameter between the proximal and distal ends that is between about 0.010 inch to 0.050 inch (0.25-1.25 mm).

8. The system of claim 1, wherein the outer jacket has a substantially uniform outer diameter between the proximal and distal ends that is between about 0.010 inch to 0.050 inch (0.25-1.25 mm).

9. The system of claim 1, wherein the core member distal portion is biased to a curved shape that extends transversely from the longitudinal axis and then curving to cross the longitudinal axis before the distal tip.

10. The system of claim 1, wherein the core wire comprises a central wire and one or more helical wires wrapped around the central wire.

11. The system of claim 1, wherein the core wire distal portion includes one or more features configured to enhance engagement or fragmentation of the distal portion with a clot.

12. The system of claim 11, wherein the one or more features comprise one or more of a plurality of bumps on the outer surface, a surface modification of the outer surface, a plurality of polymeric beads, and plurality of relatively short segments of tubing.

13. The system of claim 1, wherein the pin is configured to slide within the helical slot and rotate the distal tip relative to the outer jacket distal end while limiting movement of the distal tip between a proximal-most position and a distal-most position defined by an axial length of the helical slot.

14. A method for accessing a branch body lumen from a main body lumen to perform a procedure within a patient's body, comprising:
  providing a guidewire comprising an outer jacket including proximal and distal ends, and a core wire including a distal portion extending from the outer jacket distal end and terminating in a curved distal tip;
  introducing the guidewire into the main body lumen such that the distal portion is disposed within the main body lumen beyond the outer jacket distal end;
  directing the core wire axially relative to the outer jacket, thereby causing cooperating elements on the core wire and outer jacket to rotate the distal tip within the main body lumen until the distal tip is oriented towards the branch body lumen; and
  advancing the entire guidewire to direct the distal tip and distal portion of the core wire into the branch body lumen; and
  advancing a distal end of a tubular device over the guidewire from the main body lumen into the branch lumen.

15. The method of claim 14, wherein the branch body lumen is within the patient's neuro-vasculature.

16. A method for accessing a branch body lumen from a main body lumen to perform a procedure within a patient's body, comprising:
  providing a guidewire comprising an outer jacket including proximal and distal ends, and a core wire including a distal portion extending from the outer jacket distal end and terminating in a curved distal tip;
  introducing the guidewire into the main body lumen such that the distal portion is disposed within the main body lumen beyond the outer jacket distal end;
  directing the core wire axially relative to the outer jacket, thereby causing cooperating elements on the core wire and outer jacket to rotate the distal tip within the main body lumen until the distal tip is oriented towards the branch body lumen; and
  advancing the entire guidewire to direct the distal tip and distal portion of the core wire into the branch body lumen,
  wherein the cooperating element comprise a helical slot in the outer jacket adjacent the outer jacket distal end and a pin on the core member that is slidable in the helical slot, thereby causing the distal tip to rotate relative to the outer jacket when the core wire is directed axially.

17. The method of claim 16, wherein the helical slot has an axial length and wherein the pin limits movement of the distal tip between a proximal-most position and a distal-most position defined by the axial length.

18. A method for accessing a branch body lumen from a main body lumen to perform a procedure within a patient's body, comprising:
  providing a guidewire comprising an outer jacket including proximal and distal ends, and a core wire including a distal portion extending from the outer jacket distal end and terminating in a curved distal tip;
  introducing the guidewire into the main body lumen such that the distal portion is disposed within the main body lumen beyond the outer jacket distal end;
  directing the core wire axially relative to the outer jacket, thereby causing cooperating elements on the core wire and outer jacket to rotate the distal tip within the main body lumen until the distal tip is oriented towards the branch body lumen;
  advancing the entire guidewire to direct the distal tip and distal portion of the core wire into the branch body lumen; and
  manipulating the guidewire such that the distal portion is disposed within a blood vessel adjacent a clot;
  advancing the guidewire such a distal tip of the guidewire is introduced at least partially into the clot; and
  directing the core wire axially relative to the outer jacket, thereby causing cooperating elements on the core wire and outer jacket to rotate the distal tip to at least partially break up the clot.

19. A system for performing a thrombectomy procedure, comprising:
  an elongate tubular member comprising a proximal end, a distal end sized for introduction into a patient's vasculature, and an aspiration lumen extending there between; and
  a guidewire comprising:
    an outer jacket comprising a proximal portion, a distal portion sized for introduction into the aspiration lumen, a lumen extending there between, and one or more helical slots extending along an axial length of the outer jacket adjacent the distal end; and
    an inner core wire comprising a proximal portion extending through the lumen to the outer jacket proximal end, and a distal portion, the core wire movably disposed within the lumen of the outer jacket such that the core wire distal portion extends from the outer jacket distal portion, the core wire distal portion terminating in a curved distal tip, the core wire comprising one or more pins adjacent the core wire distal portion, each pin slidably received in a respective helical slot in the outer jacket such that axial movement of the core wire relative to the outer jacket causes the pin to slide within the helical slot and rotate the distal tip relative to the outer jacket distal portion while limiting movement of the distal tip between a proximal-most position and a distal-most position defined by the axial length.

* * * * *